US012150635B1

(12) United States Patent
Almulhim

(10) Patent No.: US 12,150,635 B1
(45) Date of Patent: Nov. 26, 2024

(54) ADJUSTABLE TRIPLE HEADS THYROID RETRACTOR

(71) Applicant: KING FAISAL UNIVERSITY, Al-Ahsa (SA)

(72) Inventor: Abdulrahman Saleh Almulhim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/377,536

(22) Filed: Oct. 6, 2023

(51) Int. Cl.
*A61B 17/02* (2006.01)

(52) U.S. Cl.
CPC ...... *A61B 17/0206* (2013.01); *A61B 17/0218* (2013.01); *A61B 2017/0287* (2013.01)

(58) Field of Classification Search
CPC ............ A61B 17/0206; A61B 17/0218; A61B 2017/0287
USPC ................................................ 600/201–245
See application file for complete search history.

(56) References Cited

U.S. PATENT DOCUMENTS

| | | | |
|---|---|---|---|
| 1,311,313 A | 7/1919 | Brix | |
| 5,339,801 A | 8/1994 | Poloyko et al. | |
| 5,667,481 A | 9/1997 | Villalta et al. | |
| 6,196,969 B1 * | 3/2001 | Bester | A61B 17/0206 600/219 |
| 7,481,766 B2 | 1/2009 | Lee | |
| 9,044,280 B1 | 6/2015 | Arambula | |
| 9,381,008 B2 | 7/2016 | Thornburg | |
| 10,070,852 B2 | 9/2018 | Mast et al. | |
| 11,109,753 B2 | 9/2021 | Weiman | |
| 2016/0081681 A1 * | 3/2016 | Waugh | A61B 34/20 606/279 |

FOREIGN PATENT DOCUMENTS

| | | |
|---|---|---|
| CN | 202179568 U | 4/2012 |
| CN | 114129209 A | 3/2022 |
| WO | 03017847 A1 | 3/2003 |

* cited by examiner

*Primary Examiner* — Eduardo C Robert
*Assistant Examiner* — Tara Rose E Carter
(74) *Attorney, Agent, or Firm* — Nath, Goldberg & Meyer; Joshua B. Goldberg

(57) ABSTRACT

A medical retraction device is constructed as a plurality of at least three arms hinged together at a hinge point, and extensions to grip a patient's tissue for retraction. Each arm has a rod portion and terminates with a retraction hook. The arms have a ratcheting function, in which linear movement of the arms effects retraction of a patient's tissue and provides for exposure of a surgical site. Finger grips extend from at least a subset of the plurality of arms and at least one of the finger grips controls the ratcheting function for that arm. In operation, the operator makes an incision and inserts retraction device so that the rod end portions extend into the incision. The operator then adjusts the arms by controlling the ratcheting.

10 Claims, 1 Drawing Sheet

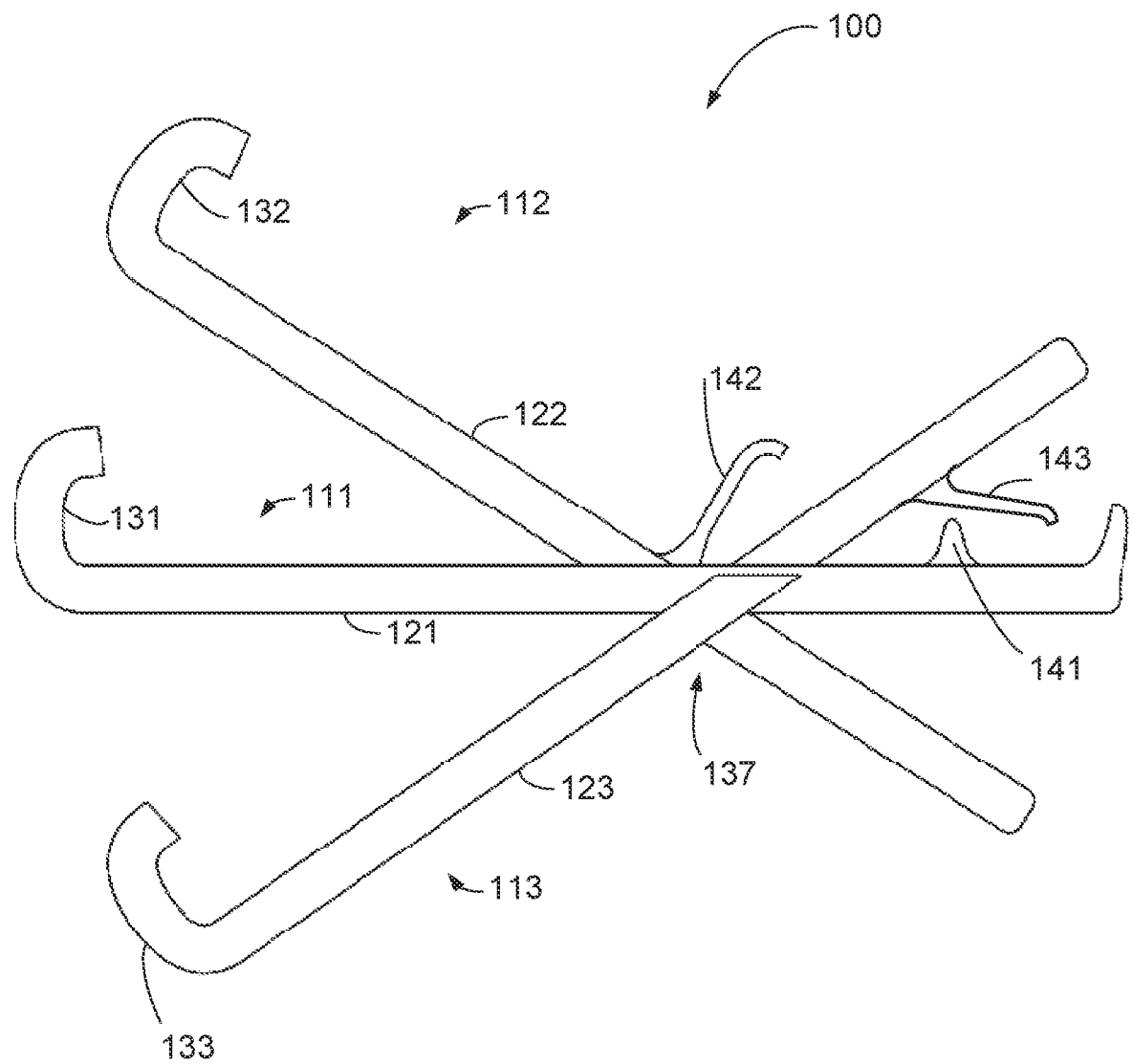

ADJUSTABLE TRIPLE HEADS THYROID RETRACTOR

BACKGROUND

Technical Field

The present disclosure relates to surgical retractors. More specifically, the disclosure is a retractor which may be used during thyroid surgery.

Background Art

Although retractors with three heads/blades are known, it is desired to provide a functionality in which adjustment of the arms is made in a facile manner.

A number of retractor arrangements are shown in the art. U.S. Pat. No. 6,196,969, to Bester et al., discloses a retractor having finger grips, side claws and a center claw. The center claw includes a ratchet sector. U.S. Pat. No. 7,481,766, to Lee et al., discloses a multiple-blade retractor having handle portions, distal portions with opposing blades and sliding bar having a blade and inner face. A locking mechanism is provided. U.S. Pat. No. 5,339,801, to Poloyko et al., shows a surgical retractor 10 having three retractor blades three blades intersecting at a linkage pin. U.S. Pat. No. 9,044,280, to Arambula, et al., discloses a retractor assembly having variable stop locks for side blades, and the use of a center blade.

SUMMARY

A medical retraction device is constructed as a plurality of at least three arms hinged together at a hinge point, and extensions to grip a patient's tissue for retraction. Each arm comprises a rod portion and terminates with a retraction hook. The arms have a ratcheting function, wherein linear movement of the plurality of arms effects retraction of a patient's tissue and provides for exposure of a surgical site. Finger grips extend from at least a subset of the plurality of arms. At least one of the finger grips controls the ratcheting function for that arm.

In operation, the operator makes an incision and inserts the retraction device so that the rod end portions extend into the incision. The operator then adjusts the arms by controlling the ratcheting, and movement of the plurality of arms effects retraction of a patient's tissue and provides for exposure of a surgical site.

BRIEF DESCRIPTION OF THE DRAWINGS

FIG. 1 is a schematic diagram showing a retraction device constructed according to a disclosed configuration.

DETAILED DESCRIPTION

Overview

There are different types of thyroid retractors used during thyroid surgery, typically requiring the need to use more than one retractor to expose the surgical field. It is noted that in some surgeries, notably thyroid surgery, it is desired to provide three heads to retract the surgical field using one tool, as currently the desired three heads are supplied using three separate tools. The disclosed technology provides a retractor for use during thyroid surgery, in which the retractor is provided with three heads in one tool, rather than three separate tools. The side retractors are each fitted with a ratchet for adjustment. The side retractors and center retractor all meet at a point of intersection at a proximal end. While thyroid surgery is described, this is presented as a non-limiting example, as the retractor can be used for retraction in a wide variety of surgeries.

The present disclosure presents a configuration for retractors with at least three heads or blades, in which the heads or blade form side arms and intersect at a proximal location. The heads or blades are fitted with ratchets for the side arms. In addition to precise control of the retractors, this provides three heads in one tool, rather than three separate tools. Since the three heads are in one tool, the retraction during surgery is facilitated, with an ability to more precisely adjust the side arms while establishing a desired distance between the retraction ends of the arms.

Construction

FIG. 1 is a schematic diagram showing a retraction device 100 constructed according to a disclosed configuration. Depicted are three arms 111, 112, 113. Arms 111, 112, 113 are constructed with respective rod portions 121, 122, 123, terminating with respective retraction hooks 131, 132, 133. Retraction hooks 131, 132, 133 function as extensions to grip the patient's tissue for retraction. Arms 111, 112, 113 are connected together at rod portions 121, 122, 123 in a bypass arrangement at intersection 137.

In the depicted non-limiting example, arms 111, 112, 113 have fixed relative angles; however, it is possible to provide position adjustments for the rod portions 121, 122, 123 to adjust the lengths of rod portions 121, 122, 123. Arms 111, 112, 113 ratchet across intersection 137, which allows direct ratcheting movement of each arm 111, 112, 113. Each arm 111, 112, 113 ratchets against one other arm, which provides a precise control of the positions of retraction hooks 131, 132, 133 without the need to provide intermediate supports for retraction hooks 131, 132, 133.

At least two of the rod portion 121, 122, 123 has extending therefrom a finger or hand grip 141, 142, 143, in order to control the ratcheting function and thereby facilitate relative movement of arms 111, 112, 113. In the present non-limiting example, arm 121 has no ratcheting function on its own, but rather one or both of arms 122 and 123 ratchet against arm 121. If both of arms 122 and 123 do not directly ratchet against arm 121, the arm that does not directly ratchet against arm 121 ratchets against the other one of arms 122 and 123.

Finger or hand grips 142 and 143 control the ratcheting function as part of a ratcheting mechanism, which gives the retractor 100 its ratcheting property by allowing relative movement in a linear direction with respect to the other rods. In use, the ratcheting is sufficient to prevent linear movement of rod portions 121, 122, 123 under the pressure of the portion of the patient's tissue being retracted, but which allows the physician to expand and close arms 111, 112, 113, either by force or by releasing the ratcheting mechanism according to design choice. The construction of the ratcheting mechanism is otherwise conventional. The ratcheting force may be adjustable or may be fixed.

In use, the surgeon makes a suitable incision, inserts retraction device 100 so that rod end portions 121, 122, 123 extend into the incision. The surgeon then adjusts arms 111, 112, 113. Movement of the plurality of arms effects retraction of a patient's tissue and provides for exposure of a surgical site.

While three arms 111, 112, 113, with associated rod portions 121, 122, 123 are described, it is possible to construct the retraction device with more than three arms. It is also possible to configure the relative movement of rod portions 121, 122, 123 to be angularly adjusted slide the adjustable angle, in which case the ratcheting function and retraction force are provided by the sliding.

While fixed relative angles of rod portions 121, 122, 123 are described, it is possible to configure the retraction device 100 so that an angular adjustment of rod portions 121, 122, 123 is possible.

CLOSING STATEMENT

It will be understood that many additional changes in the details, materials, steps and arrangement of parts, which have been herein described and illustrated to explain the nature of the subject matter, may be made by those skilled in the art within the principle and scope of the invention as expressed in the appended claims.

What is claimed is:

1. A medical retraction device comprising:
    a plurality of at least three arms connected together in a predetermined angular relationship in a bypass arrangement, each of said arms comprising a fixed rod portion and terminating with a retraction hook; and
    a ratcheting mechanism on at least one of the arms allowing linear movement of each of said plurality of at least three arms relative to the other arms,
    wherein a length of the fixed rod portions of each of the plurality of three arms is adjustable,
    wherein the predetermined angular relationship of the fixed rod portions of each of the plurality of three arms is adjustable, and
    wherein movement of the plurality of arms is adapted to effect retraction of a patient's tissue and provides for exposure of a surgical site.

2. The medical retraction device of claim 1, further comprising three of said arms, each arm terminating with one of said retraction hooks.

3. The medical retraction device of claim 1, further comprising:
    three of said arms, each arm terminating with one of said retraction hooks; and
    at least a subset of the fixed rod portions having, extending therefrom, a finger or hand grip in relative movement of the arms, with at least one of the finger grips controlling the ratcheting mechanism for that arm.

4. The medical retraction device of claim 1, further comprising:
    three of said arms, each arm terminating with one of said retraction hooks;
    at least a subset of the fixed rod portions having, extending therefrom, a finger or hand grip in relative movement of the arms; and
    at least a subset of the fixed rod portions having, extending therefrom, a finger or hand grip in relative movement of the arms, with at least one of the finger grips controlling the ratcheting mechanism for that arm.

5. The medical retraction device of claim 4, wherein, in use:
    the operator makes an incision and inserts the retraction device so that an end of the fixed rod portions are adapted to extend into the incision,
    the operator adjusts the arms by controlling the ratcheting; and
    movement of the plurality of arms is adapted to effect retraction of a patient's tissue and provides for exposure of a surgical site.

6. The medical retraction device of claim 1, further comprising:
    three of said arms, each arm terminating with one of said retraction hooks;
    the fixed rod portions having, extending therefrom, a finger or hand grip in relative movement of the arms; and
    at least a subset of the fixed rod portions having, extending therefrom, a finger or hand grip in relative movement of the arms, with at least one of the finger grips controlling the ratcheting mechanism for that arm.

7. The medical retraction device of claim 6, wherein, in use:
    the operator makes an incision and inserts retraction device so that an end of the fixed rod portions are adapted to extend into the incision,
    the operator adjusts the arms by controlling the ratcheting; and
    movement of the plurality of arms is adapted to effect retraction of a patient's tissue and provides for exposure of a surgical site.

8. The medical retraction device of claim 1, wherein, in use:
    the operator makes an incision and inserts retraction device so that an end of the fixed rod portions are adapted to extend into the incision,
    the operator adjusts the arms by controlling the ratcheting; and
    movement of the plurality of arms is adapted to effect retraction of a patient's tissue and provides for exposure of a surgical site.

9. A medical retraction device comprising:
    retraction means comprising a plurality of at least three arms connected together in a predetermined angular relationship in a bypass arrangement, said retraction means allowing linear movement of each of said plurality of at least three arms relative to the other arms, each of said arms comprising a fixed rod portion and terminating with a retraction hook, and a ratcheting function, wherein a length of the fixed rod portions of each of the plurality of three arms is adjustable, wherein the predetermined angular relationship of the fixed rod portions of each of the plurality of three arms is adjustable, and wherein linear movement of the plurality of arms is adapted to effect retraction of a patient's tissue and provides for exposure of a surgical site;
    finger grip means extending from at least a subset of the plurality of arms; and
    at least one of said finger grip means controlling the ratcheting function.

10. The medical retraction device of claim 9, wherein, in use:
    the operator makes an incision and inserts retraction device so that an end of the fixed rod portions are adapted to extend into the incision,
    the operator adjusts the arms by controlling the ratcheting; and
    movement of the plurality of arms is adapted to effect retraction of a patient's tissue and provides for exposure of a surgical site.

* * * * *